United States Patent [19]

Sarstedt et al.

[11] Patent Number: 4,687,479

[45] Date of Patent: Aug. 18, 1987

[54] BLOOD STORAGE DEVICE

[75] Inventors: Walter Sarstedt, Nümbrecht-Rommelsdorf; Dieter Korf, Nümbrecht-Winterborn, both of Fed. Rep. of Germany

[73] Assignee: Walter Sarstedt Kunststoff-Spritzgusswerk, Fed. Rep. of Germany

[21] Appl. No.: 798,761

[22] Filed: Nov. 15, 1985

[30] Foreign Application Priority Data

Nov. 20, 1985 [DE] Fed. Rep. of Germany ....... 3442423

[51] Int. Cl.$^4$ .............. A61B 19/00

[52] U.S. Cl. .............. 604/403; 604/256

[58] Field of Search .............. 604/405, 411, 415, 256; 206/306-307

[56] References Cited

U.S. PATENT DOCUMENTS

| | | | |
|---|---|---|---|
| 2,388,634 | 11/1945 | Woody | 604/415 |
| 3,005,455 | 10/1961 | Poitras et al. | 604/415 |
| 3,944,104 | 3/1976 | Watson et al. | 215/307 |
| 4,007,639 | 2/1977 | Haeckel | 73/425.4 P |
| 4,133,462 | 1/1979 | Lindström | 215/307 |
| 4,328,828 | 5/1982 | Cianci | 604/405 |
| 4,377,248 | 3/1983 | Stull | 215/306 |
| 4,392,055 | 7/1983 | Whitney | 215/307 |
| 4,460,101 | 7/1984 | Tseng | 215/307 |

FOREIGN PATENT DOCUMENTS

| | | | |
|---|---|---|---|
| 1153132 | 8/1963 | Fed. Rep. of Germany | 604/415 |
| 2439218 | 6/1977 | Fed. Rep. of Germany . | |
| 2943747 | 5/1981 | Fed. Rep. of Germany | 215/307 |
| 1545591 | 10/1968 | France | 215/307 |

*Primary Examiner*—C. Fred Rosenbaum
*Assistant Examiner*—Sherri E. Vinyard
*Attorney, Agent, or Firm*—Townsend and Townsend

[57] ABSTRACT

A blood storage device consists of a blood extraction tubule (20) and a removable cover (12) which closes its upper opening. The cover (12) consists of a closure member (21) with a small opening (14) and a slider (13) arranged in the closure member (21) by means of which the passage of air from the inner space (17) of the blood extraction tubule (20) through the opening (14) can be interrupted.

14 Claims, 6 Drawing Figures

BLOOD STORAGE DEVICE

Figure 1:
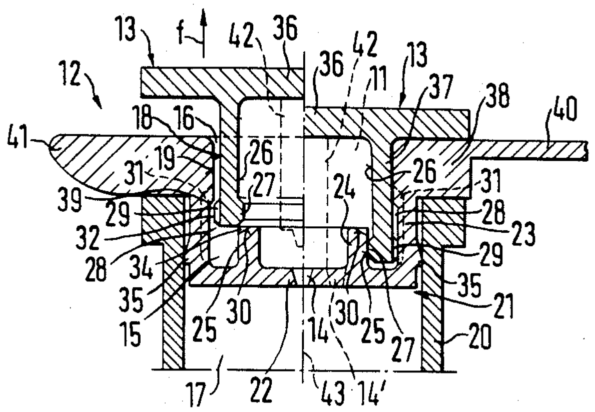

The invention relates to a blood storage device comprising a blood accommodating tubule having a capillary-like mouthpiece at one end and an opening with a substantially larger diameter at the other end, said opening being sealingly closable by a removable cover.

In a known blood storage device of this kind (German Auslegeschrift No. 24 39 218) the blood accommodating tubule has a capillary mouthpiece for the extraction of the smallest quantities of blood. A right cylindrical tube unitarily adjoins the mouthpiece and is made broader relative to the mouthpiece in such a way that it permits the insertion of a micropipette and can be closed by means of a plug at its broadened end. In accordance with the invention described there the removable cover is preferably formed as a plug.

If such blood storage devices are handled during or after the extraction of blood the danger exists that blood can run out of the broadened end if the blood accommodating tubule is inclined too far. It is not possible to counteract this by the placement of a cover during the taking of blood but only after the taking of blood. However, the placement of the cover after the taking of blood must be done in a separate working step and blood can be spilled due to the large upper opening of the blood extraction tubule. During the taking of blood the cover generally hangs on the tubule by means of a lug. A hermetic closure after the taking of blood can be problematic and indeed initially undesirable if a pressure balance is to be possible between the interior of the blood extraction tubule and the atmosphere. During this time the cover may not yet have been set in place, so that the spillage of blood is possible.

The object underlying the invention is to provide a blood storage device of the initially named kind in which the emergence of blood from the upper end of the tube need not be feared if it is held in an inclined position, but in which venting of the tubule is nevertheless possible, and in which, after the taking of blood, a complete closure of the upper end of the blood extraction tube can be effective at any time without the danger of blood being spilled, but in which a pressure balance between the interior of the blood extraction tubule and the atmosphere is also possible for a certain period of time.

In order to satisfy this object the invention provides that the cover comprises a closure member which is sealingly and remoably arranged at the blood accommodating tubule and a slider which is closed at the top by a cover plate, which can be arranged in a hollow chamber on the side of the closure member facing away from the blood accommodating tubule, and which can be displaced between an open position and a closed position; that, in the open position, the slider leaves a narrow passage between the blood storage chamber and the atmosphere which merely acts as a vent, but does not permit the passage of blood when the blood accommodating tubule is inclined; and that the slider sealingly recloses this passage when in the closed position.

The thought underlying the invention is thus to be seen in the fact that the cover, which consists of two parts, itself represents an externally actuatable valve which makes it possible to interrupt the narrow connection which is initially present between the interior space of the blood accommodation tubule and the atmosphere. For this purpose the passage which is initially present should be sufficiently small and arranged in such a way that on inclining the tubule, so that blood would run out if a cover were not present, this is avoided because of the arrangement and narrowness of the opening.

The opening should thus permit the passage of air but not of blood.

It is basically also possible to provide several small openings alongside one another.

As a result of the construction in accordance with the invention the closure member can already be set in place during manufacture so that it does not get in the way during the taking of blood. If the interior of the blood accommodating tubule is then to be hermetically sealed against the outside the valve is closed by pushing the slider into the closure member.

A particularly good and hermetic closure of the cover after the taking of blood can be obtained if a spigot is provided on the slider which sealingly engages in the preferably central opening only when the slider is pressed down (pressed in).

An advantageous practical realisation of the invention is characterised in that the hollow chamber is of substantially right cylindrical shape and in that the slider is of complementary shape in such a way that the slider is displaceable in piston-like manner between the open position and the closed position. In this way a simple actuation of the valve of the invention is made possible because the slider is preferably displaceable in the axial direction within the closure member into the closed portion in the manner of a piston.

A further preferred embodiment is characterised in that the base wall of the closure member which separates the hollow chamber from the inner chamber contains a small opening; and that a sealing projection extends away from the base wall, radially spaced from the peripheral wall of the closure member, axially inwardly into the hollow chamber, with the outer wall of the sealing projection being in sealing engagement with the slider when the latter is in the closed position.

Furthermore, it is advantageous if the slider has an annular bead at its radially inner side in the lower end region of the inner wall.

In addition it is expedient if at least one air passage in flow connection, on the one hand, with the atmosphere and, on the other hand, with the small opening adjacent the inner chamber is provided between the cylinder walls of the slider and of the closure member; and if an air passage is present between the sealing projection and the slider when the latter is in the open position. The small opening can with this arrangement also be eccentrically arranged in the closure member so that even larger inclined angular positions are possible before the blood located in the tubule reaches the small opening.

A particularly preferred embodiment of the invention is so constructed that the slider is connected in hinge-like manner via a flexible lug with the upper end of the blood accommodating tubule. In this manner there is no danger that the slider is pressed into the closed position, from which it cannot be removed, or can only be removed with difficulty, prior to the taking of blood. If however the slider and the closure member are sufficiently far apart from one another prior to and during the taking of blood, which is made possible by the flexible lug, the danger of premature closure of the valve does not exist.

In order to make separation of the slider from the closure member more difficult, and thus to force the removal of the closure member including the slider when opening the blood extraction tube, a further embodiment provides that the cover plate of the slider does not project radially beyond the closure member when the slider is in the closed position, in such a way that the slider cannot any longer be straightforwardly separated from the closure member but rather so that only the closure member can be removed from the upper end of the blood accommodating tubule.

It is particularly advantageous in this connection if a recess is provided in the upper surface of the closure member into which the cover plate of the slider enters in the closed position, in such a way that, after putting together the closure member and the slider, it is no longer possible for the operator to have access beneath the cover plate.

Since the blood extraction tubule is already largely closed both during and after the extraction of blood, although not closed in gas-tight manner, provision can be made in accordance with a further preferred embodiment for a mixing ball to be loosely arranged in the interior of the blood accommodating tubule, with the diameter of the ball being larger than that of the small opening in the closure member. As a result of the arrangement of the closure member of the invention the mixing ball cannot fall out of the upper end of the blood accommodating tubule when it is shaken.

A further advantageous embodiment is characterised in that the capillary mouthpiece of the blood accommodating tubule is sealingly closable by a closure cap which is pushed onto it and which is laterally secured prior to use to the closure member or to the colour plate via a desired break region. This construction avoids the relatively small closure cap being lost before it is used after the taking of blood, because the cap is fixedly connected with a part of the cover.

It is also expedient if the cover plate of the slider is flat at its upper side and is capable of being written on. This construction makes is possible to provide the labelling necessary during the taking of blood samples without problem on the top side of the cover plate.

Finally, a further embodiment is so constructed that the blood accommodating tubule is arranged in a centrifuge adapter tube in such a way that the closure cap stands on the base of the centrifuge adapter tube and a securing ring at the upper end of the blood accommodating tubule sits beneath an upper end flange thereof on the upper end edge of the centrifuge adapter tube. In this manner a good retention of the blood accommodating tubule within the adapter tube of the centrifuge is ensured.

Figure 2:
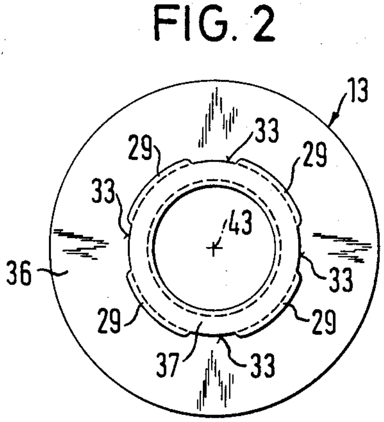

The invention will now be described in the following by way of example only and with reference to the drawings which show:

FIG. 1 an axial section through the upper part of a blood storage device in accordance with the invention, with the open position of the slider being shown in the left hand part of the representation and with the closed position of the slider being shown in the right hand half, FIG. 2 a view from below of the slider used in the blood storage device of the invention, FIG. 3 a view from above the closure member of the blood storage device of the invention, FIG. 4 a partly sectioned side view of a further embodiment of a blood storage device in accordance with the invention, with the blood storage device being arranged inside a centrifuge adapter tube, FIG. 5 a reduced side view of the subject of FIG. 4 with the slider in the closed position, and FIG. 6 a plan view of the subject of FIG. 5 to an enlarged scale with the closure cap still present thereon.

As seen in FIG. 1 the upper opening of a blood extraction tube 20, which has a capillary mouthpiece which is not shown at its bottom end (46 in FIG. 4), is closed at the top by a cover 1. The cover 12 consists of a closure member 21 with an annular sealing bead 35 which is inserted into the blood extraction tube 20 from above in plug-like manner, and a slider 13 which is accommodated in a hollow chamber 11 of the closure member 21 in the manner of a piston.

The hollow chamber 11 is of substantially right cylindrical shape, with the axis 43 of this cylinder being aligned with the axis of the blood extraction tube 20. The slider 13 consists of an upper flat cover plate 36 which projects radially on all sides in flange-like manner beyond the upper edge of the slider 13, but does not however project radially beyond the edge of the closure member 21. Furthermore, the slider 13 has a cylindrical portion 37 which extends into the hollow chamber 11. The cylindrical portion 37 has, at its lower end, a radially inwardly projecting annular sealing bead 27 and a radially outwardly projecting abutment bead 29 which, as seen in FIG. 2, has interruptions 33 which are displaced relative to one another by 90° in each case.

The closure member 21 has a peripheral wall 23 which carries the sealing bead 35 and a peripheral flange 38 at the top which sits on the edge of the blood extraction tubule 20. At the bottom the closure member 21 is closed by a base wall 22 which, as shown in FIG. 1, has a small opening 14 at the center which connects the hollow chamber 11 with the inner chamber 17 of the blood extraction tubule 20. The small opening 14 could also be eccentrically arranged at the position 14' indicated in broken lines. This would have the advantage that, if the blood extraction tubule 20 were tilted to the left in FIG. 1, the blood contained in the tubule would only reach the opening 14 at a larger angle of inclination.

In accordance with the invention a sealing projection 24 which has the form of a cylinder extends concentrically upwardly away from the base wall 22. The sealing projection 24 finishes at approximately one third of the total height of the closure member 21. Radially outwardly directed chamfers 30 are located on the sealing projection 24 at the upper edge. An annular chamber 15 is located between the annular projection 24 and the peripheral wall 23 of the closure member 21 and is substantially aligned with the cylindrical wall 37 of the slider 13. The diameter of the cylindrical wall 37 of the slider 13 is somewhat smaller than the diameter of the hollow chamber 11 in the upper region of the closure-member 21 so that an axial air passage 16 is present between the slider 13 and the closure member 21, at least when the slider 13 is in the open position (left hand half of FIG. 1). In other words a clear spacing exits between the outer wall 18 of the slider 13 and the inner wall 19 of the upper region of the closure member 21 whereby the air passage 16 is formed.

The outer wall 25 of the sealing projection 24 and the inner side 26 of the cylindrical wall 37 are substantially aligned with one another. The inner annular sealing bead 27 however overlaps the outer wall 25 somewhat in a radially inward direction. However, the annular sealing bead 27 is somewhat chamfered at its bottom end so that it can slide along the outer wall 25 of the sealing projection 24 when the slider 13 is pressed down, and indeed with a small degree of radical compression.

In the lower half of the closure member 21 the hollow chamber 11 has a radially outwardly extending broadened region 28. This means that the hollow chamber 11 is clearly broadened downwardly via an annular step 39 substantially before the sealing projection 24. The abutment bead 29 is arranged within this broadened portion 28. Its extent in a radially outward direction is such that it overlaps with the inner wall 19 of the flange 38 and is thus secured by the ring step 39 against being drawn out in the direction of the arrow f in FIG. 1.

The interruptions 33 between the abutment beads 29 (FIG. 2) serve to ensure an air passage even when the slider 13 is slid downwardly to the closed position as shown in FIG. 1. This is necessary so that the air can escape outwardly from the annular chamber 15.

Instead of providing interruptions 33 in the abutment bead 29 broadened regions 31 which are shown in FIG. 1 in broken lines, and which take on the air guiding function, could also be provided in the wall of the hollow chamber 11 in the region of the broadened portion 28. In principle it would be sufficient if such broadened portions 31 or interruptions 33 are only provided at a few points of the periphery.

In any case the abutment bead 29 should have a small radial distance from the wall of the hollow chamber 11 so that an air passage 32 is also present between the wall and the abutment bead 39 at positions where no interruptions 33 are present.

Figure 3:
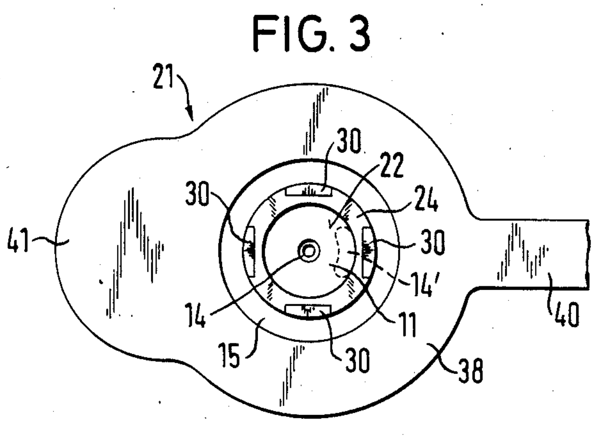

As seen in FIGS. 1 and 3 the closure member 21 has a lug 40 at its flange 38 which is only partially illustrated and by means of which the closure member can be resiliently and movably secured to a suitable position of the blood extraction tubule 20. The lug can however also be omitted, in accordance with the invention, because the cover sits from the very outset on the tubule 20.

A handle or handling lug 41 is located at the diametrically opposite side of the closure member and facilitates the actuation and in particular the removal of the closure member 21 from the blood extraction tubule 20.

The manner of operation of the blood storage device in accordance with the invention is as follows:

The closure member 21 can already be inserted in the factory into the position shown in FIG. 1 with the valve open (left hand position of the slider 13 in FIG. 1). In this position blood can be picked up through the mouthpiece provided at the opposite end of the blood extraction tubule 20. The air which is displaced by the entry of the blood into the blood extraction tubule 20 can escape outwardly into the atmosphere through the small opening 14, through the hollow chamber 11, past the chamfers 30, through the annular chamber 15, through the air passage 32 and finally through the air passages 16. Even when the blood extraction tubule 20 is largely filled and is somewhat tilted no blood can emerge from the top because the small opening 14 is much too small to permit the passage of blood. Even if small drops of blood should enter into the hollow chamber they will be retained there and cannot reach the outside.

If the upper end of the blood extraction tube 20 is now to be hermetically closed then the slider is displaced by the exertion of pressure thereon in the opposite direction to the arrow f into the closed position illustrated in the right hand half of FIG. 1, whereby the annular bead 27 slides along the outer wall 25 of the sealing projection 24 and the lower part of the cylindrical wall 37 broadens somewhat in resilient manner. In this way a hermetic seal is obtained between the annular sealing bead 27 and the sealing projection 24. The resilient broadening can extend sufficiently far that the abutment bead 29 of FIG. 1 abuts against the interior boundary of the peripheral wall 23. The dimensioning is such that when the slider 13 has been pressed downwardly its cover plate 36 lies flat on the upper surface of the flange 38 of the closure member 21 so that the opening of the valve is only possible with difficulty.

Whereas in the drawing the entire diameter of the upper part of the closure member 21 has been made larger in order to form the air passage 16 it would also be possible to provide only axial grooves in this region in the inner wall 19 or in the outer wall 18 for the axial guidance of air.

In the depressed state of the slider 13 the blood extraction tubule 20 is hermetically closed and it can now be transported without the danger of blood escaping.

If one wishes to remove the blood sample from the blood extraction tube 2 then the closure member 21 including the slider 13 is removed from the upper opening by means of the lug 41, whereupon the blood sample can be poured out or pipetted in the customary manner.

In a simplified embodiment a spigot 42 (shown in broken lines FIG. 1) could be attached to the slider 13 which sealingly closes the opening 14 in the closed state.

In the following embodiment, which will be described with reference to FIGS. 4 to 6, the same reference numerals are used to described parts which have counterparts in FIGS. 1 to 3.

Figure 4:
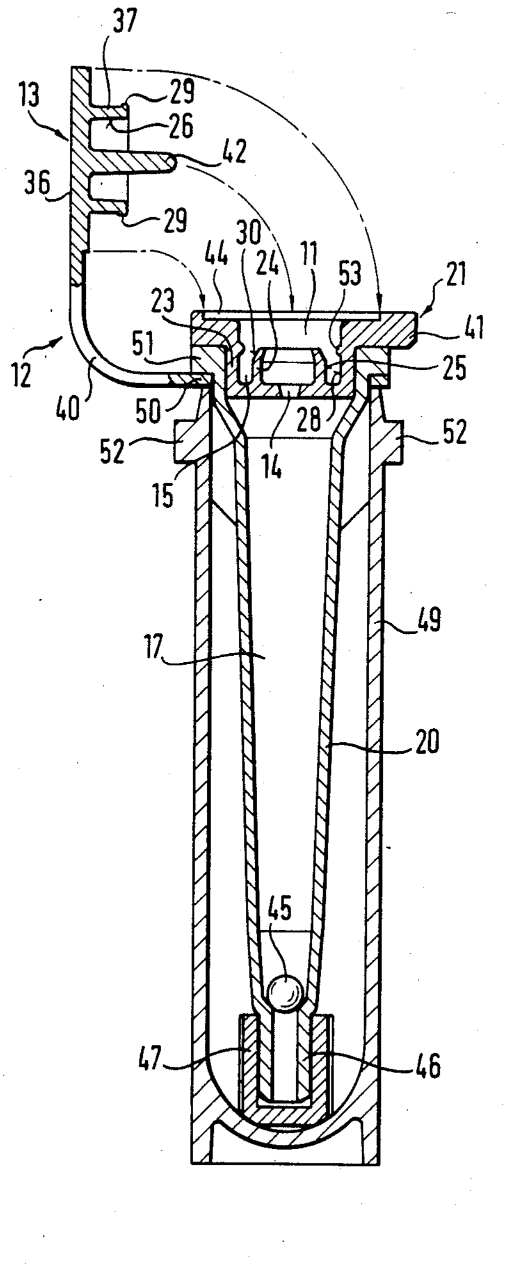
Figure 5:
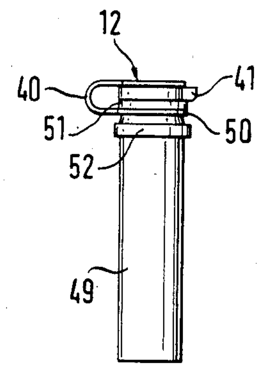

As seen in FIGS. 4 and 5 the slider 13 with the closure plate 36 is connected via a flexible lug 40 with the upper end of the blood extraction tube 20, with the lug 40 being in one piece with a ring 50 which surrounds the upper end of the blood extraction tube 20 beneath a radially outwardly projecting flange 51.

An annular disk-like recess 44 which is complementary to the shape of the cover plate 36 is provided in the upper surface of the closure member 21. In this way the closure plate 36 is arranged in recessed manner when the slider 13 is placed onto the closure member 21. It is thus no longer possible to lift the closure plate 36 away again from the closure member 21. In order to open it, it is on the contrary necessary to grasp the closure member 21 at the handle 41. In advantageous manner the closure member 21 is connected with the lug 40 via the slider 13 after removal of the closure member 21 from the blood extraction tube, so that the cover 12 which now consists of the parts 13, 21 cannot be lost.

As the slider 13 is not connected with the closure member 21 during the taking of blood, other than through the lug 40, the capillary bore 14 is sufficient for venting, whereas the cylinder wall 37 enter into a sealed snap engagement with the closure member 21 via the annular latching beads 29 and 53, respectively.

As seen in FIGS. 4 and 5 the blood extraction tubule 20 is arranged in a centrifuge adapter tube 49 which can be suspended in a centrifuge, not shown, by means of an upper annular projection 52. At the top the ring 50 which is located beneath the flange 51 lies on the upper edge of the centrifuge adapter tube 49.

The capillary mouthpiece 46 which is located at the bottom of the blood extraction tubule 20 is sealingly closed from below by a cap-like closure cap 47 which can be pushed into place from below. In the state in which it is inserted in the centrifuge adapter tube 49 the closure cap 47 sits on the floor of the centrifuge adapter tube 49. The blood extraction tubule 20 is thus supported in troublefree manner for the centrifuging process.

A mixing ball 45 is located in the interior of the blood extraction tubule 20 and has a diameter which is substantially greater than that of the small opening 14 so that on shaking the blood extraction tubule 20 the ball thoroughly mixes the content of the blood extraction tube 20, but can not escape from the tubule. The possibility of providing the mixing ball 45 in the interior of the blood extraction tubule 20 represents a further substantial advantage of the placement of the closure member 21 during and after the extraction of blood.

Figure 6:
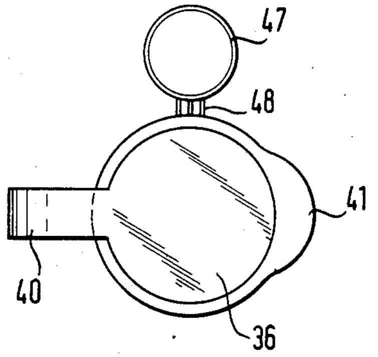

As seen in FIG. 6 the closure cap 47 is first secured to the side of the cover plate 36 or preferably of the closure member 21 via a desired break region 48. The closure cap 47 is thus held until it is needed in such a way that cannot be lost. As soon as the extraction of blood has been completed the closure cap 47 can be separated from the closure member 21 by twisting or tearing and can be used to close the capillary mouthpiece 46.

Furthermore, it can be seen from FIGS. 4 to 6 that the upper surface of the cover plate 36 is flat and is made so that it can be written on.

The inner diameter of the capillary mouthpiece is 1.5 mm. In this way better throughmixing is achieved; moreover, the danger of the capillary mouthpiece becoming blocked does not exist.

The spherically rounded base of the centrifuge adapter tube 49 has proved to be particularly favourable.

The small venting bore 14 in the closure member 21 has a diameter of approximately 1 mm.

A particulate advantage of the small venting bore 14 lies in the fact that the extrusion of blood automatically stops when the blood extraction tube 20 has been filled with blood up to the venting bore. The further extraction of blood, which likewise takes place by capillary action, is automatically interrupted.

Should, however, in certain cases, blood emerge through the small bore 14, then it is at most the inner chamber of the cylindrical sealing projection 24 which fills with blood and an outwardly projecting lobe of blood forms at the upper opening of the sealing projections 24, which is clearly narrowed by conical contraction of the upper edge of the sealing projection 24 relative to the internal diameter of the sealing projection 24, but is still larger than the vent bore 24, with the outwardly projecting lobe of blood then preventing a further outflow of blood as a result of surface tension effects.

The mixing ball 45 consists of plastic with a high density.

After the taking of blood the closure cap 47 is first pushed onto the capillary mouthpiece 46. Only then is the slider 13 with the cover plate 36 which is to be labelled pushed into the closure member 21.

We claim:

1. A blood storage device comprising:

a tubule having a capillary-like mouthpiece at a lower end for receiving blood and an opening of substantially larger diameter than that of said mouthpiece at an upper end, said opening being sealably closable by a removable cover;

a closure member having a cylindrical section sized to fit inside said tubule in a sealing and removable manner, a flange extending peripherally from the top of said cylindrical section of sufficient width to cover the rim of the said tubule, a base wall at the bottom of said cylindrical section with an opening of sufficiently small diameter to substantially prevent the passage of blood while permitting the passage of air;

a sliding element comprising a cylindrical projection sized to pass through said flange into the interior of said cylindrical section of said closure member, said sliding element having a range of travel between an upper limit and a lower limit, a flat plate covering the top of and extending radially beyond said cylindrical projection while terminating within the circumference of said flange, a bead extending outward from said cylindrical projection, a stop extending inward from said closure member to engage said bead when said sliding element is at said upper limit, and a sealing projection extending upward from said base wall into the interior of said cylindrical section and radially spaced therefrom, the outer wall of said sealing projection sealingly engaging said cylindrical projection when said bead is at said lower limit.

2. A blood storage device in accordance with claim 1 in which said stop is an inverted shoulder on the interior surface of said cylindrical section of said closure member.

3. A blood storage device in accordance with claim 1 in which said stop is an interrupted bead on the interior surface of said cylindrical section of said closure member.

4. A blood storage device in accordance with claim 1 further comprising a plug positioned on said sliding element to seal said opening of said base wall when said sliding element is in a closed position.

5. A blood storage device in accordance with claim 15 in which said cylindrical section is a right circular cylinder and said sliding element is complementary thereto in shape whereby said sliding element is displaceable within said cylindrical section in piston-like manner between an open position and a closed position.

6. A blood storage device in accordance with claim 1 further comprising a circumferential bead at the lower end of the interior surface of said cylindrical projection of said sliding element.

7. A blood storage device in accordance with claim 1 further comprising an air vent between said cylindrical section of said closure member and said cylindrical projecton of said sliding element, communicating said opening with the atmosphere; and an air passage between said sealing projection and said sliding element when said sliding element is in the open position.

8. A blood storage device in accordance with claim 1 further comprising a flexible lug connecting said sliding element in hinge-like manner with said upper end of said tubule. .

9. A blood storage device in accordance with claim 1 further comprising a recess in the upper surface of said closure member sized to receive said flat plate of said sliding element and thereby prevent access to the underside of said flat plate.

10. A blood storage device in accordance with claim 1 further comprising a mixing ball loosely retained in the interior of said tubule, said mixing ball having a diameter larger than that of said opening in said base wall of said closure member.

11. A blood storage device in accordance with claim 1 further comprising a closure cap sized to fit over said mouthpiece in sealingly closable manner, said closure cap being laterally secured to said closure member through a breakable connection.

12. A blood storage device in accordance with claim 1 further comprising a closure cap sized to fit over said mouthpiece in sealingly closable manner, said closure cap being laterally secured to said flat plate of said sliding element through a breakable connection.

13. A blood storage device in accordance with claim 12 further comprising a centrifuge adapter tube having an open end, sized to receive said tubule, said centrifuge adapter tube containing a base adapted to engage said closure cap when the latter is placed over said mouthpiece, and said tubule further contains a flange around its upper end sized to rest upon the rim at said open end of said centrifuge adapter tube.

14. A blood storage device in accordance with claim 1 in which said sealing projection is cylindrical and tapered at its upper end leaving an internal opening, both the internal diameter of said sealing projection and said internal opening being of a diameter greater than that of said opening on said base wall.

* * * * *